United States Patent
Myers

(10) Patent No.: US 6,764,977 B2
(45) Date of Patent: Jul. 20, 2004

(54) SAFE, FREE-FLOWING SOLID PEROXIDE COMPOSITIONS

(75) Inventor: Terry Ned Myers, Phoenixville, PA (US)

(73) Assignee: ATOFINA Chemicals, Inc., Philadelphia, PA (US)

( * ) Notice: Subject to any disclaimer, the term of this patent is extended or adjusted under 35 U.S.C. 154(b) by 597 days.

(21) Appl. No.: 09/804,705

(22) Filed: Mar. 13, 2001

(65) Prior Publication Data

US 2001/0044497 A1 Nov. 22, 2001

Related U.S. Application Data

(60) Provisional application No. 60/190,795, filed on Mar. 21, 2000.

(51) Int. Cl.$^7$ ............................. B01J 21/18; B01J 27/20; C01B 15/00
(52) U.S. Cl. ...................... 502/160; 502/170; 502/171; 502/174; 252/186.23; 252/186.26; 252/186.42; 568/567
(58) Field of Search .................. 525/263, 386, 525/265, 387; 502/160, 170, 171, 174; 106/287.24; 252/186.23, 186.26, 186.42; 568/951, 558, 559, 567; 526/228, 227, 232.5

(56) References Cited

U.S. PATENT DOCUMENTS

4,197,215 A * 4/1980 Dudinyak .................... 502/170
5,066,726 A * 11/1991 Modic ........................ 525/263

FOREIGN PATENT DOCUMENTS

JP 11-302310 * 11/1999

* cited by examiner

*Primary Examiner*—Michael La Villa
(74) *Attorney, Agent, or Firm*—William D. Mitchell

(57) ABSTRACT

Safety stabilized solid, free-flowing compositions based on t-butyl peroxy maleic acid as well as processes for their preparation and use are disclosed.

6 Claims, No Drawings

SAFE, FREE-FLOWING SOLID PEROXIDE COMPOSITIONS

This application claims the benefit of Provisional Application No. 60/190,795, filed Mar. 21, 2004.

BACKGROUND OF THE INVENTION

This invention relates to compositions of t-butyl peroxymaleic acid containing solid diluents and methods of using these compositions in polymer modification; more particularly this invention relates to compositions of dry, solid, free-flowing solid peroxyesters having melting points greater than 30° C., and certain salts of organic acids having melting points greater than the melting points of the peroxides to which they are added, with optionally a dust suppressant, and optionally a free-flowing aid.

In particular, this invention comprehends processes for modifying polymer and copolymer compositions, by using the solid peroxide formulations to graft monomers, attach peroxide decomposition products, or intentionally degrade the polymer or copolymer (for example, such reactions known as vis-breaking, controlled rheology, or rheology modification).

PRIOR ART

Many diluted peroxide compositions are described in the prior art, although none of them teaches the instant invention.

U.S. Pat. No. 3,538,011 describes solid, free-flowing, stabilized compositions containing organic peroxides and organic fillers and the methods for the production of these compositions. Organic peroxides employed in this patent for these organic peroxide/organic filler compositions are aromatic and aliphatic diacyl peroxides, ketone peroxides and peroxyesters that are solid at room temperature whereas, the fillers employed are solid plasticizers that are soluble in polyester resin masses and are solid at room temperature, such as dicyclohexyl phthalate (m.p. 63–5° C.). These organic fillers are claimed to reduce the explosiveness and the shock sensitivity of the organic peroxides employed.

U.S. Pat. No. 4,387,044 describes safe, dry, free-flowing solid peroxide/unsubstituted or alkyl substituted benzoic acid compositions prepared by mixing the solid peroxide, such as a diacyl peroxide, dialkyl peroxydicarbonate, dialkyl peroxide or alkylidene diperoxide, which melts about 30° C. with solid benzoic acid or an alkyl substituted benzoic acid, which melts above 40° C. The patent teaches that these compositions are useful as initiators for the polymerization of ethylenically unsaturated monomers, such as styrene, and for curing of unsaturated polyester resins and diethylene glycol bis(allyl carbonate). The solid peroxide compositions exhibit improved safety characteristics such as delayed ignition times when in contact with flame and increased thermal stabilities compared to prior art formulations.

U.S. Pat. Nos. 2,453,070 and 2,453,071 disclose impact shock-desensitized dibenzoyl peroxide compositions in which the preferred compositions are desensitized with 2–10% aliphatic carboxylic acids such as lauric acid and less preferably desensitized with 5% phthalic acid and 5% salicylic acid.

The prior art also is replete with many peroxide paste compositions containing one or more organic safety liquids and water. Although these peroxide pastes and suspensions are described to be safe, none of them teach a safe, free-flowing solid peroxide composition of the present invention that have been found to be significantly more permanently stable than similar prior art formulations and considerable more resistant to burning ignition. Moreover, the filler in the instant invention has no detrimental effects on the rate of solution of, or the polymerization or curing efficiency of the formulation in ethylenically unsaturated monomers, such as styrene or in unsaturated polyester resins.

None of the above art references describes the instant invention. Although t-butyl peroxymaleic acid is mentioned in two of the references, no examples were described using this peroxide. Yet there is still a need for appropriate commercial formulations of t-butyl peroxymaleic acid. This is primarily due to safety and handling considerations. Packaging and shipping regulations for this peroxide restrict transport of pure t-butyl peroxymaleic acid to 25 kilogram packages for safety reasons (see *Recommendations on the Transport of Dangerous Goods, Model Regulations*, 10$^{th}$ revised edition, United Nations, New York, 1997). This makes using this peroxide on a commercial scale difficult, since large quantities must be purchased and stored and handled in relatively small packages. A viable alternative is to formulate diluted peroxide that exhibits safety characteristics that will permit shipment and handling of larger quantities. As the prior art indicates, there are many possible diluents, yet no one diluent meets the needs of all end use applications. The instant invention is for novel, extended formulations of t-butyl peroxymaleic acid that are acceptable for use in many commercial applications.

SUMMARY OF THE INVENTION

This invention provides a safe, free-flowing, solid, peroxide formulation consisting essentially of 40–85% by weight of solid t-butyl peroxymaleic acid, 15–60% by weight of a solid diluent selected from salts of structure $(R-CO_2)_x M^{(+x)}$ wherein x is an integer selected from 1, 2 or 3 and wherein R is a linear or branched alkyl group of 5–30 carbon atoms optionally substituted with one or more hydroxy (—OH) groups, or a linear or branched mono-, di- or polyalkenyl group of 5–20 carbons and when x is 1, M is a metal ion chosen from lithium, sodium, potassium, and when x is 2, M is a metal ion chosen from calcium, magnesium, lead, barium, cadmium and zinc, and when x is 3, M is aluminum, salts of structure $CO_2(M^{(+x)})_y$ wherein x and y are integers selected from 1 or 2, wherein when y is 1, x is 2 and M is a metal ion selected from calcium, magnesium, lead, barium, cadmium and zinc, and when y is 2, x is 1 and M is a metal ion selected from lithium, sodium, potassium, and optionally 0–2% by weight of a dust suppressant, and optionally 0–2% of a free-flowing aid. Hydrates of the salts may be used. Mixtures of salts may be used.

DETAILED DESCRIPTION OF THE INVENTION

It has now been discovered that a free-flowing, flowing, solid t-butyl peroxymaleic acid composition can be significantly safer with respect to burning ignition and thermal stability than previous free-flowing, solid compositions of the prior art.

A. Solid Diluent of Structure (R—CO2)xM(+x)

Calcium Stearate

Zinc Stearate

Magnesium Stearate

Sodium Stearate

Potassium Stearate

Aluminum Stearate (1:3)
Tin Stearate
Lead stearate
Calcium Oleate
Zinc Oleate
Magnesium Oleate
Sodium Oleate
Potassium Oleate
Calcium Laurate
Zinc Laurate
Magnesium Laurate
Sodium Laurate
Potassium Laurate
Calcium Palmitate
Zinc Palmitate
Magnesium Palmitate
Sodium Palmitate
Potassium Palmitate
Calcium Montanate
Calcium Caprylate
Zinc Caprylate
Sodium Caprylate
Potassium Caprylate
Potassium Sorbate
Calcium Valerate
Zinc Valerate
Calcium Myristate
Zinc Myristate
Magnesium Myristate
Zinc Caproate
Calcium Caproate
Sodium Caproate B. Solid Diluents of Structure $CO_2(M(+x))y$ Calcium Carbonate
Magnesium Carbonate
Lead Carbonate
Barium Carbonate
Cadmium Carbonate
Zinc Carbonate
Lithium Carbonate
Sodium Carbonate
Potassium Carbonate C. Optional Dust Suppressants Suitable optional dust suppressants for the inventive compositions are liquid such as mineral spirits or mineral oils having flash points above 100° F., sucrose acetate isobutyrates and liquid plasticizers such as benzyl butyl phthalate, dibutyl phthalate and tricresyl phosphate.

D. Optional Free-flowing Aids

Suitable optional free-flowing aids for the inventive compositions are solids such as silicas such as micronized microcrystalline silica, fumed silica, sodium zirconium silica hydrogel, calcium silicate, silicon dioxide, microcrystalline cellulose, carbonates such as sodium carbonate or calcium carbonate, phosphates, such as tricalcium phosphate, sodium sulfonates such as sodium diisopropylnaphthalenesulfonate, sodium polyalkylnaphthalenesulfonate, sodium aluminosilicate, and talc.

E. Methods for Preparation of Solid Peroxide Compositions

Several procedures can be employed to prepare the solid, free-flowing peroxide/diluent compositions of this invention:

Procedure 1

Wetted granular peroxide can be blended or mixed with an appropriate amount of a solid, granular diluent and optionally with an appropriate amount of dust suppressant and optionally with an appropriate amount of free-flowing aid, until a uniform mixture is obtained. Then the mixture can be tray-dried or dried by other methods known in the art.

Procedure 2

To a stirred aqueous slurry of granular peroxide are added an appropriate amount of a solid, granular diluent, optionally with an appropriate amount of dust suppressant and optionally with an appropriate amount of free-flowing aid. A surfactant can also be optionally added to aid in forming a uniform aqueous slurry. After stirring for about 5 to 10 minutes, the solid is obtained by filtration or centrifugation and the wetted solid mixture is then dried.

Procedure 3

To a slurry of the granular peroxide containing an organic solvent such as pentane, hexane, toluene, mineral spirits, etc. is added the solid diluent and optionally a dust suppressant and optionally containing a free-flowing aid, The resulting slurry is stirred for 5 to 10 minutes and the product is obtained by initially filtering or centrifuging solvent.

Procedure 4

Granular, dry, solid peroxide and diluent are hand-mixed for about 15 minutes or until uniform.

The optionally-employed surfactant can be any non-ionic surfactant such as a nonylphenoxy polyethoxyethanol, anionic surfactant such as an alkali salt of an alkylaryl polyether sulfonate or a cationic surfactant such as an alkyldimethylbenzylammonium halide in which the alkyl group contains 10 to 20 carbons.

Utility

The inventive peroxide compositions are useful as free-radical initiators in the bulk, emulsion, solution or suspension polymerization or copolymerization of ethylenically unsaturated monomers at suitable temperatures and pressures. Temperatures of 20° C. to 250° C., preferably 30° C. to 200° C. and peroxide levels (on a pure basis) of 0.005% to 3%, preferably 0.01% to 1%, by weight based on monomer, are normally employed in these polymerization processes. Ethylenically unsaturated monomers include olefins such as ethylene, propylene, styrene, alpha-methylstyrene, chlorostyrene, vinyltoluene, vinylbenzyl chloride, vinyl pyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid, methacrylic acid and their esters and amides, such as methyl, ethyl, n-butyl and 2-ethylhexyl acrylates and methacrylates, and acrylamide and methacrylamide; maleic anhydride; maleic and fumaric acids and their esters, vinyl halo and vinylidene halo compounds, such as vinyl chloride, vinyl bromide, vinyl fluoride, vinylidene chloride, vinylidene fluoride; perhaloolefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, diallyl phthalate, allyl ethyl carbonate, triallyl phosphate, diallyl fumarate and diallyl carbonate; acrolein; methyl vinyl ketone; and mixtures thereof.

The solid, free-flowing peroxide/diluent compositions of this invention are also useful for the curing of unsaturated polyester resin compositions. Unsaturated polyester resins that can be cured by the compositions of this invention usually consist of an unsaturated polyester and one ro more polymerizable monomers. The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, allylsuccinic acid, tetrahydrophthalic acid and others with saturated or unsaturated di- or polyols, such as ethylene glycol, diethylene glycol, triethylene glycol, 1,2- and 1,3-propanediols,1,2-, 1,3- and 1,4-butanediols, 2,2-dimethyl-1,3-propanediols,2-hydroxymethyl-2-methyl-1,3-propanediol, 2-buten-1,4-diol, 2-butyn-1,4-diol, 2,2,4-trimethyl-1,3-pentanediol, glycerol, Bisphenol A, mannitol and others. Mixtures of such polyacids and/or mixtures of such polyols may also be used. The unsaturated di- or polycarboxylic acids may be partly replaced by saturated polycarboxylic acids, such as adipic acid, succinic acid, sebacic acid and others and/or by aromatic polycarboxylic acids, such as phthalic acid, trimellitic acid, pyromellitic acid, isophthalic acid and terephthalic acid. The acids may be substituted by groups such as halogen. Examples of suitable halogenated acids are, for example, tetrachlorophthalic acid, 1,2,3,4,7,7-hexachlorobicyclo(2.2.1)hept-2-ene-5,6-dicarboxylic acid and others. The other component of the unsaturated polyester resin composition, the polymerizable monomer or monomers, can be preferably ethylenically unsaturated monomers, such as styrene, chlorostyrene, vinyltoluene, divinylbenzene, alpha-methylstyrene, diallyl maleate, diallyl phthalate, dibutyl fumarate, acrylonitrile, triallyl phosphate, triallyl cyanurate, methyl acrylate, methyl methacrylate, n-butyl methacrylate, ethyl acrylate and others, or mixtures thereof, which are co-polymerizable with said polyesters. A preferred resin composition contains as the polyester component the esterification product of 1,2-propylene glycol (a polyol), maleic anhydride (an anhydride of an unsaturated polycarboxylic acid) and phthalic anhydride (an anhydride of an aromatic dicarboxylic acid) as well as the monomer component, styrene. Temperatures of about 10° C. to 200° C. and peroxide levels of about 0.055 to 5% or more by weight of curable unsaturated polyester resin are normally employed. The unsaturated polyesters described above can be filled with various materials such as sulfur, glass fibers, carbons blacks, silicas, metal silicates, clays, metal carbonates, antioxidants, heat and light stabilizers, sensitizers, dyes, pigments, accelerators, metal oxides, such as zinc oxide, blowing agents, etc.

In addition, the free-flowing, solid peroxide compositions of this invention can be employed for vulcanizing natural and synthetic rubbers, for curing of olefin copolymers and terpolymers, such as EPR (ethylene-propylene copolymers) and EPDM (ethylene-propylene-terpolymer), for crosslinking of polyethylene, ethylene-vinyl acetate copolymers, silicon rubbers, styrene-butadiene rubbers and the like, in the presence of absence of additives and fillers such as sulfur, carbon blacks, silicas, clays, carbonates, antioxidants, heat and light stabilizers, sensitizers, dyes, accelerators, zinc oxide, oils, blowing agents, etc.

Other types of unsaturated resins can be cured using the compositions of this invention as curing catalysts. These resins, call unsaturated vinyl ester resins, consist of a vinyl ester resin component and one or more polymerizable monomer components. The vinyl ester resin component can be made by reacting chloroepoxide such as epichlorohydrin with appropriate amounts of a glycol such as Bisphenol A, in the presence of a base such as sodium hydroxide, to yield a condensation product having terminal epoxy groups derived from the epichlorohydrin. Subsequent reaction of the condensation product with polymerizable unsaturated carboxylic acids such as acrylic acid and methacrylic acid, in the presence or absence of acidic or basic catalysts, results in the formation of a vinyl ester-terminated resin component. Normally styrene is added as the polymerizable monomer component to complete the preparation of the unsaturated vinyl ester resin. Temperatures of about 10° C. to 200° C. and pure peroxide levels of about 0.05% or more by weight of curable unsaturated vinyl ester resin compositions are normally employed for curing the unsaturated vinyl ester resins. The unsaturated resin described above can be filled with the materials employed with the unsaturated polyester resin compositions previously described.

This invention also encompasses the use of the inventive peroxide formulations in:

(i) a process for curing an elastomer resin, including an elastomer resin without unsaturation, by heating the resin and about 0.001% by weight to about 10% by weight of a novel peroxide compound of this invention at a temperature effective to cure the elastomer resin;

(ii) a process for crosslinking an olefin polymer by heating a non-crosslinked olefin polymer and about 0.001% by weight to about 10% by weight of a novel peroxide compound of this invention at a temperature effective to crosslink the olefin polymer resin;

(iii) a process for reducing the molecular weight of a propylene polymer and modifying the molecular weight distribution of a propylene polymer, by heating a propylene polymer that is a polypropylene or propylene copolymer and about 0.001% by weight to about 5% by weight of a novel peroxide compound of this invention to a temperature effective to reduce the molecular weight and to modify the molecular weight distribution of the propylene polymer; and optionally up to 1% by weight of molecular oxygen can be employed as a modification co-catalyst; and (iv) a process for attaching peroxide decomposition products to olefin polymer or copolymer by heating the olefin polymer or copolymer and about 0.001% by weight to about 10% by weight of a novel peroxide compound of this invention at a temperature effective to decompose the peroxide (as described in U.S. Pat. No. 5,447,985 and incorporated herein by reference).

Temperatures of about 140° C. to 340° C. are normally employed. Other polymers that can be modified by the instant peroxide formulations include low density polyethylene (LDPE), linear low density polyethylene (LLDPE), high density polyethylene (HDPE), etc. Unlike modification or PP and propylene copolymers, modification of these other polymers with the instant peroxides usually results in chain extension, melt flow index reduction, melt viscosity increase and molecular weight increase.

A particular advantage exists for peroxides formulations containing the inventive diluents in that many process for polyolefin modification already involve the use of the solid diluent in the peroxide formulation. The means that the user of the peroxide formulation will not have to account for any new chemicals in their process. This is a distinct advantage in that no new components are introduced that might affect the final properties of the modified polyolefin, such as physical properties (tensile, color, melting behavior), weathering behavior or thermal stability. Metallic stearates are probably the most widely used lubricants in polyolefin modification due to their ability to promote fusion, provide good internal lubrication and enhanced mold release (F. Axel, Modern Plastics Encyclopedia, November, 1998, p C-23).

The following Examples further illustrate the best mode contemplated by the Inventor for the practice of the Invention.

EXAMPLE 1

Solid t-butyl peroxymaleic acid, 85.0 g, 95% assay (based on active oxygen analysis), was weighed into a 500 ml beaker. Calcium carbonate, 15.0 g (Fisher Scientific, 99.9% assay) was added, and the solids blended together using a plastic spatula for five minutes until the mixture appeared uniform. The resultant solid blend was analyzed to contain 81% PMA.

EXAMPLE 2

Solid t-butyl peroxymaleic acid, 85.0 g, 95% assay (based on active oxygen analysis), was weighed into a 500 ml beaker. Calcium stearate, 15.0 g (Stavinor, 99.9% assay) was added, and the solids blended together using a plastic spatula for five minutes until the mixture appeared uniform. The resultant solid blend was analyzed to contain 81% PMA. Safety improvement

| | Peroxide Formulations | | |
|---|---|---|---|
| Safety Tests | Pure Peroxide | Example 1 | Example 2 |
| Rapid Heat Decomposition Temperature, °C., type | 112 rapid | 113 moderate | 110 moderate |
| Pressure Vessel Test, Vent Diameter, mm | >1, <3 | >1, <3 | <1 |
| Hot Iron Test, propagation of decomposition in a 2 g sample, seconds | 4 | 10 | 28 |

The data demonstrate the greatly improved safety characteristics of the diluted peroxide formulations.

I claim:

1. A free-flowing, solid, peroxide/diluent formulation comprising:

40–85% by weight of solid t-butyl peroxymaleic acid,

15–60% by weight of a solid diluent selected from the group consisting of: salts of structure $(R-CO_2)_xM$ wherein x is an integer equal to 1, 2 or 3 and wherein R is a linear or branched alkyl group of 5–30 carbon atoms optionally substituted with one or more hydroxy (—OH) groups, or a linear or branched mono-, di- or polyalkenyl group of 5–20 carbons and when x is 1, M is a metal ion selected from the group consisting of lithium, sodium, potassium and mixtures thereof, and when x is 2, M is a metal ion selected from the group consisting of calcium, magnesium, lead, barium, cadmium, zinc, and mixtures thereof and when x is 3, M is the metal ion derived from aluminum, and salts of structure $(CO_2)My$, wherein y is an integer equal to 1 or 2 wherein when y is 1, M is a metal ion selected from the group consisting of calcium, magnesium, lead, barium, cadmium, zinc and mixtures thereof and when y is 2, M is a metal ion selected from the group consisting of lithium, sodium and potassium, mixtures and hydrates thereof, 0–2% by weight of a dust suppressant, and 0–2% by weight of a free-flowing aid.

2. A solid peroxide composition of claim 1 wherein the solid diluent is selected from the group consisting of calcium stearate, zinc stearate or sodium stearate.

3. A solid peroxide composition of claim 2 comprising about 80% t-butyl peroxymaleic acid and about 20% calcium stearate.

4. A solid peroxide composition of claim 1 wherein the dust suppressant is 0.5% mineral oil.

5. A solid peroxide composition of claim 1 wherein the free-flowing agent is 0.5% amorphous silica.

6. A solid peroxide composition of claim 1 comprising 80% t-butyl peroxymaleic acid, 19% calcium stearate, and 1% silica.

* * * * *